Figure 1:
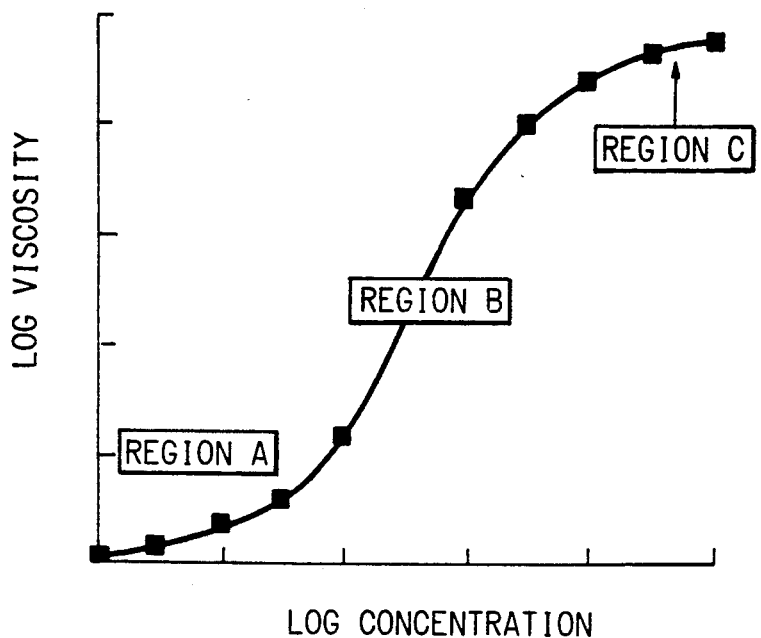

United States Patent [19]
Rennie et al.

[11] Patent Number: 5,286,405
[45] Date of Patent: Feb. 15, 1994

[54] POLYMER-THICKENED LIQUID ABRASIVE CLEANING COMPOSITIONS

[75] Inventors: George K. Rennie, Wirral, Great Britain; Neil P. Randle, Schwetzingen, Fed. Rep. of Germany

[73] Assignee: Lever Brothers Company, Division of Conopco, Inc., New York, N.Y.

[21] Appl. No.: 915,829

[22] PCT Filed: Nov. 27, 1990

[86] PCT No.: PCT/GB90/01837
§ 371 Date: Jul. 28, 1992
§ 102(e) Date: Jul. 28, 1992

[87] PCT Pub. No.: WO91/08283
PCT Pub. Date: Jun. 13, 1991

[30] Foreign Application Priority Data
Nov. 28, 1989 [GB] United Kingdom ............... 8926904.7

[51] Int. Cl.$^5$ .......................... C11D 3/22; C11D 3/37; C11D 17/00
[52] U.S. Cl. .............. 252/174.17; 252/174; 252/174.18; 252/174.23; 252/174.24; 252/174.25; 252/DIG. 2; 252/DIG. 14
[58] Field of Search ............. 252/174.23, 174.24, 252/DIG. 2, 174.17, 174.18, 174.14, 174.25, 174, DIG. 14

[56] References Cited

U.S. PATENT DOCUMENTS

| | | | |
|---|---|---|---|
| 2,594,273 | 4/1952 | Mellwig | 106/206 |
| 3,941,728 | 3/1976 | Solenberger. | |
| 3,970,594 | 7/1976 | Claybaugh | 252/524 |
| 3,996,152 | 12/1972 | Edwards et al. | 252/186 |
| 4,017,411 | 4/1977 | Diehl et al. | 252/186 |
| 4,017,412 | 4/1977 | Bradley | 252/186 |
| 4,105,461 | 8/1978 | Racciato | 106/205 |
| 4,226,736 | 10/1980 | Bush et al. | 252/135 |
| 4,260,528 | 4/1981 | Fox et al. | 252/525 |
| 4,312,675 | 1/1982 | Pickens et al. | 106/171 |
| 4,344,931 | 8/1982 | Aguilar | 424/52 |
| 4,394,179 | 7/1983 | Ellis et al. | 134/7 |
| 4,483,782 | 11/1984 | Cox et al. | 252/174.17 |
| 4,540,510 | 9/1985 | Karl | 252/315.3 |
| 4,568,555 | 2/1986 | Spanier | 426/582 |
| 4,569,782 | 2/1986 | Disch et al. | 252/106 |
| 4,585,815 | 4/1986 | Ono et al. | 524/23 |
| 4,643,840 | 2/1987 | Brocklehurst et al. | 252/160 |
| 4,675,351 | 6/1987 | Brown | 524/20 |
| 4,678,606 | 7/1987 | Akhter et al. | 252/542 |
| 4,732,692 | 3/1988 | Zabotto et al. | 252/106 |
| 4,808,324 | 2/1989 | Periard et al. | 252/23 |
| 4,820,380 | 4/1989 | O'Callaghan et al. | 162/135 |
| 4,822,500 | 4/1989 | Dobson, Jr. et al. | 252/8.551 |
| 4,826,504 | 5/1989 | Clare et al. | 8/561 |
| 5,126,066 | 6/1992 | Torenbeek et al. | 252/95 |

FOREIGN PATENT DOCUMENTS

| | | |
|---|---|---|
| 0017149 | 10/1980 | European Pat. Off. . |
| 58-213709 | 12/1983 | Japan . |
| 620828 | 12/1980 | Switzerland . |
| 1478398 | 6/1977 | United Kingdom . |
| 1514630 | 6/1978 | United Kingdom . |
| 1562275 | 3/1980 | United Kingdom . |
| 2086923 | 5/1982 | United Kingdom . |
| 2110698 | 6/1983 | United Kingdom . |
| 2163766 | 3/1986 | United Kingdom . |
| 86/03937 | 7/1986 | World Int. Prop. O. . |

OTHER PUBLICATIONS
Chemical Abstract No. 106(10):69197u, 1986.

Primary Examiner—Paul Lieberman
Assistant Examiner—A. Hertzog
Attorney, Agent, or Firm—Ronald A. Koatz

[57] ABSTRACT

A liquid composition includes an aqueous medium containing surfactant and a thickening mixture with particulate abrasive dispersed in the thickened mixture The thickening mixture comprises a synergistic mixture of a linear polymer and a branded starch polymer. The composition may be a household cleaner or a toothpaste.

12 Claims, 3 Drawing Sheets

TYPICAL LOG VISCOSITY VS LOG CONCENTRATION PLOT FOR AN AQUEOUS POLYMER SOLUTION

TYPICAL LOG VISCOSITY VS LOG CONCENTRATION PLOT FOR AN AQUEOUS POLYMER SOLUTION

TYPICAL SIGMOID CURVE FOR A GUM-TYPE POLYMER JAGUAR HP60 AT pH 9-10

POLYMER-THICKENED LIQUID ABRASIVE CLEANING COMPOSITIONS

This invention relates to aqueous liquid abrasive compositions which include detergent and means for thickening the liquid. Particulate abrasive is suspended in the liquid.

Such compositions currently on the market as household cleaning materials have a liquid phase which includes a combination of detergent and electrolyte chosen so that the detergent is present in lamellar phase and thereby causes thickening of the liquid.

It is commonplace, in very many areas of industry to use thickening agents to impart a certain rheological behaviour to liquid media. By thickening such liquid media, they can be made more suitable for their end-use, or they can be made more suitable as an intermediate medium in which other substances can be included which need to remain stably suspended or dispersed in the media. By varying the levels of thickening agents, the degree of thickening can be controlled.

A vast number of thickening agents is known in the art, and many of them have found practical application. Since frequently, however, the thickening agent does not contribute anything more than a thickening effect, one attempts to use as little as possible of the thickening agent, since these thickening agents may be rather expensive. In addition, frequently such thickening agents may be adversely affected by other substances present in the liquid media, e.g. electrolyte salts, which imposes restrictions on their use for particular purposes.

It is well known in the field of organic, polymeric thickening agents that, in general, the viscosity of a liquid is dependent on the concentration of thickening agent in that liquid. This relationship can be expressed schematically as a sigmoid curve as shown in FIG. 1 which is a plot of log viscosity vs log concentration for the thickening agent in the given liquid. While not wishing to be bound by any theory, we believe that in region A the molecules are essentially independent of one another, the viscosity increase arises from disruption of flow of the continuous phase, and the rate of increase is relatively small. In region B the molecules are sufficiently close together to interact, entangle etc., and the viscosity rises very steeply. In region C the units are close packed and increasingly experience compression so that once again the rate of increase in viscosity is relatively small.

Region A is defined as that portion of the sigmoid curve where the viscosity of the total system corresponds approximately to that of the base system and there is a linear relationship between log viscosity and log concentration.

Region B (lower) is defined as that portion of the sigmoid curve which obeys a power law relationship (the coefficient of which is greater than 1) beneath the point of inflexion.

Region B (upper) is defined as that portion of the sigmoid curve which obeys a power law relationship (the coefficient of which is greater than 1) above the point of inflexion.

Region C is defined as that portion of the sigmoid curve where the viscosity of the total system is greater than that of the base system and there is an essentially linear relationship between log viscosity and log concentration.

The point of inflexion for the sigmoid curve is defined as that point where the first derivative of the curve experiences a turning point.

For a given liquid medium the position of the sigmoid curve on the log viscosity vs log concentration graph will depend on, for example, polymer type or temperature. It is therefore convenient to describe such a system in terms of a single master curve which represents the actual measured parameter plus a shift factor which superposes the measured curve on the reference curve.

Figure 2:
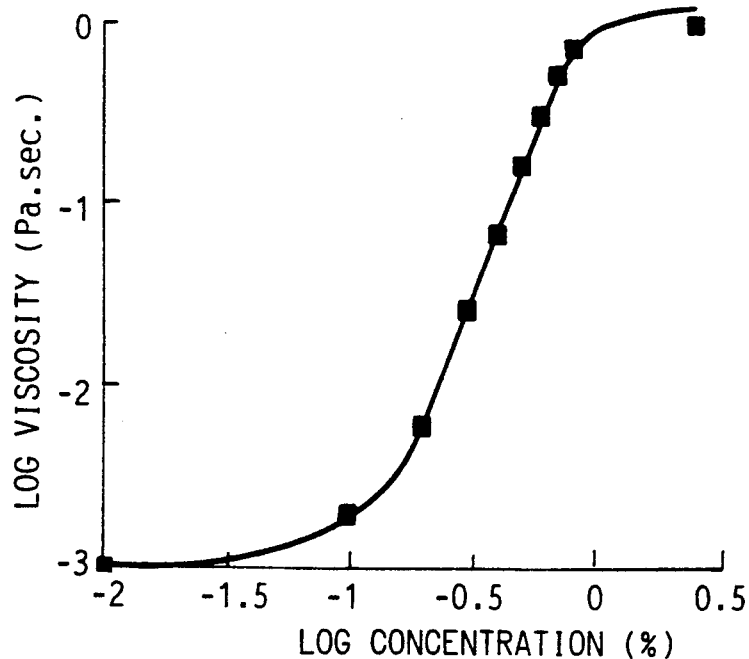

Reference sigmoid curves can be constructed according to the method described in R Simha and L Utracki, J Polymer Sci, A-2, 5, 853 (1967), L Utracki and R Simha, J Polymer Sci A, I, 1089 (1963) and R Simha and L Utracki, Rheol. Acta, 12, 455 (1973), for a liquid medium comprising a gum-type polymer. A typical sigmoid curve for the system is shown in FIG. 2 which is a plot of log viscosity vs log concentration for Jaguar HP60, which is a cellulose derived polymer.

According to the present invention there is provided an aqueous liquid abrasive cleaning composition comprising an aqueous liquid medium containing detergent and a thickening mixture, with particulate abrasive suspended in the thickened liquid medium, the detergent being present in an amount of 0.02 to 20 wt % based on the liquid medium the particulate abrasive being present in an amount of 1 to 70wt % based on the liquid medium, and the thickening mixture being present in an amount of 0.01 to 10 wt % based on the liquid medium and comprising a linear non-starch polymer and a branched starch polymer, wherein the concentration of each of the said polymers is selected according to that polymer's respective sigmoid curve of log viscosity vs log concentration for the said liquid medium, each polymer being selected from its sigmoid curve's lower portion having an increasing or substantially constant gradient, the liquid system having a viscosity of at least 20 mPa-sec at a shear rate of 10 sec$^{-1}$ greater than that of the liquid medium in the absence of the said thickening mixture.

In liquid compositions so formulated a synergistic thickening effect can be achieved. We have found that embodiments of the compositions according to the present invention show synergistic thickening together with shear-thinning, thus providing good flow properties. It is to be understood however that the present invention also extends to pastes thickened by the present thickening mixture.

Moreover, compositions of this invention show other unexpected advantages such as good physical stability as well as improved cleaning and reduced abrasion damage, particularly on soft substrates, and can show an improved rinsability when compared with current liquid abrasive cleaners.

Starches are natural polysaccharides consisting of D-glucose units. Starches contain linear molecules in which glucose units are joined by (1)→(4) alpha glucosidic linkages, and also branched molecules in which some glucose units are joined by (1)→(6) alpha glucosidic linkages thus creating chain branching. Linear starch is also known as amylose. Branched molecules are known as amylopectin. The proportion of branched molecules in starch varies somewhat with the origin of the starch.

By "branched starch polymer" we mean a starch type polymer in which at least 70% of the constituent material is molecules which are branched. Preferably at least 85% of the branched starch type polymer is provided by branched molecules. Cross linking may additionally be present. The molecular weight of the branched starch type polymer is preferably more than 1,000,000 and can be up to 2,000,000. Such materials are available commercially. More than one material can be present contributing to the branched starch type polymer. Starch type polymers are derived from natural plant sources such as maize, tapioca and potatoes.

The linear non-starch polymer can either be a synthetic polymer or it can be a polymer derived from natural sources. Synthetic polymer or the polymers in a mixture of synthetic linear polymers, may have an average molecular weight of more than 50,000, preferably more than 500,000, up to a preferred upper limit of about 10,000,000. Examples of suitable substantially linear synthetic polymers include polyvinylalcohol, polyacrylate and polyvinylpyrrolidone.

Non-starch substantially linear polymers derived from natural sources include primarily gum-type polymers. Gums, or mucilages as they are sometimes called, are basically polysaccharides (different from starch) with varying polymerization degrees. Unlike starch, any one gum can contain a variety of saccharide units e.g. glucose, mannose, fructose, galactose and generally each saccharide unit is linked to its neighbour by a (1)→(4)—beta glucosidic linkage. Gums are very high molecular weight polymers and normally have a molecular weight between 1,000,000 and 2,000,000.

Gums include the polysaccharide hydrocolloids, which are usually prepared from gums, and they may have been chemically modified, e.g. by partial acetylation, to make them more water-soluble and/or stable in the presence of other ingredients in the liquid media. Biopolymers also belonging to this class of polysaccharide hydrocolloids are known thickening agents. Typical examples of commercially available, gum-type thickening agents are xanthan gums and their derivatives which retain the polysaccharide backbone structure but incorporate chemical modification. These include a partially acetylated xanthan gum, "Kelzan" ex Kelco Company of N.J., USA, Maxaflo xanthan gum ex International Bio-Synthetics, Enorflo-XA, xanthan gum ex Shell Chemicals Ltd., and Rhodapol, a xanthan gum ex Rhone-Poulenc SA. A further example is the biopolymer Alphaflo, a succinoglucan ex International Bio-Syntehtics. Yet other gum-type thickening agents are those derived from guar gums, such as the Jaguar (R) products ex Stein, Hall and Co Inc. and those derived from cellulose such as carboxymethyl or hydroxyethyl cellulose. Cellulose is made up from glucose units but is distinguished from linear starch in that the glucose units are joined by (1)→(4) betaglucosidic links.

Thus the linear non-starch polymer may be one or a mixture of xanthan gums, guar gums, succinoglucan gums, cellulose, and derivatives of any of these which include the polysaccharide polymer chain thereof.

Gum-type thickening agents have been described in our European Patent Application 0 174 689, published on 19 Mar. 1986, in which representative thickening agents have been described for inclusion in shear-thinning liquid cleaning compositions. This publication is hereby incorporated by way of reference.

Where the linear polymer is derived from natural sources, such as in the case of xanthan gum, the present invention can thus provide a synergistic polymer thickening system which is derived wholly from natural materials. The thickening components can thus both be derived from naturally renewable sources and be environmentally degradable. We have also found that the present use of a combination of naturally derived polymer thickening agents can leave the liquid system naturally opaque, which can eliminate the need for the addition of artificial opacifiers.

In the ideal case the sigmoid curves for each polymer will be as shown in FIG. 1. The lower portion of the curve from which the present polymers must be selected thus corresponds in the ideal case to region A and region B (lower), subject to the limitation that sufficient polymers must be present to effect and increase in the system of at least 20 cPs at a shear rate of 10 sec $^{-1}$. In practice when the present curves are constructed for a variety of polymers not all polymers follow an ideal sigmoid curve. An overall sigmoid shape can be discerned allowing the presently defined lower portion to be identified i.e. that portion having a constant or increasing gradient and extending between a point near the origin along the curve until the gradient begins to decrease. In some instances however region C may in effect be non-existent as the viscosity at such concentrations may be too high to measure readily or alternatively region C may include a second point of inflextion. In the latter instance it is only the lower portion of the curve up until the first point of inflexion from which the polymer should be selected. Another non-ideal variant in the shape of the sigmoid curve may include a region of substantially constant gradient between region B (lower) and region B (upper). Such region would fall within the present definition of the lower portion of the curve from which the present polymers must be selected.

It should be noted moreover that the sigmoid curves to be employed are those measured according to the liquid medium in question, i.e. the log viscosity vs. log concentration plot of each polymer is that of the polymer in the presence of any other ingredients which might be present in the liquid medium.

Preferably the relative weight ratio of the linear non-starch polymer to the branched starch polymer in the thickening mixture ranges from 50:1 to 1:100, preferably from 20:1 to 1:25 and more preferably from 5:1 to 1:15. The amount of thickening agent used in total for thickening liquid media ranges between 0.01 and 10 wt %, more preferably from 0.1 to 10% by weight of the liquid medium. Yet more preferably it is from 0.25 to 5% by weight of the liquid medium. It may be from 0.25 to 5% by weight of the final product.

The invention has the added advantage that by altering the variables of a given system it is possible to manipulate otherwise unsuitable polymers into the A region or B (lower) region of their sigmoid curve and obtain the synergistic benefit. A preferred means of altering the systems is by addition of an electrolyte to the liquid medium.

The present compositions can include a liquid medium which includes an electrolyte. A preferred level of electrolyte is 0.1 to 10 wt % electrolyte with respect to the liquid medium.

For a particular system the synergistic increment can be calculated according to the equation given below $$S = \left[ \frac{\eta(P_1 + P_2)}{\eta P_1 + \eta P_2} - 1 \right] \times 100$$

where S—the synergistic increment $\eta(P_1+P_2)$ = the viscosity of a mixture of polymers $P_1$ and $P_2$ $\eta P_1$ = the viscosity of polymer $P_1$ $\eta P_2$ = the viscosity of polymer $P_2$ Preferably the thickening mixture imparts a synergistic increment S of at least 5%, more preferably a synergistic increment of at least 10%, even more preferably a synergistic increment of at least 50%.

The synergistic increment S is thus a measure of the increase in viscosity in a liquid medium containing polymeric thickening agents in accordance with the present invention over and above what might otherwise be expected having regard to the sum of the respective contributions made to the viscosity by each polymer measured separately. In as much as it is known (see for example "Polymeric Stabilisation of Colloidal Systems" by Donald H Napper Academic Press Inc 1983) that mixtures of polymers in a liquid medium frequently separate and show incompatibility resulting in the liquid media separating into layers, it is, we believe surprising that the polymeric thickening system of the present invention not only provides a cumulative effect in terms of increased viscosity, but additionally has an apparent synergistic element in increasing the resultant viscosity yet further. The present invention thus permits not only increased flexibility in choice of thickening polymeric agent, but also, if desired, permits cost savings to be made with regard to the amount of polymeric thickening agent required. Not only can the total amount of polymeric thickening agent be reduced relative to the use of a single polymeric thickening agent, but for example in a two component polymeric thickening system a minor amount of the more expensive polymeric thickening agent may be able to exert a disproportionate effect in the total system.

Compositions of this invention contain 0.02 to 20 wt % of detergent, based on the liquid medium. Thickening with a synergistic mixture of this invention has the advantage of giving a wider choice of detergent than when the detergent is required to form a lamellar phase to enhance viscosity.

The preferred amount of detergent is at least 0.05 wt %, more preferably 0.1 to 15 wt % and even more preferably 1 to 10 wt %. The detergent active material can be selected from the group comprising anionic, nonionic, zwitterionic, cationic detergents and mixtures thereof.

Notably the detergent may comprise soap and/or synthetic anionic detergent materials such as alkylbenzenesulphonates, alkanesulphonates, alkylsulphates, alkylethersulphates and mixtures thereof.

A household cleaner may include nonionic detergent, and the amount of this may be 0.1 to 10 wt %.

Compositions of this invention contain suspended particular abrasive materials. We have found that liquid abrasive household cleaners embodying the present invention and containing 30 to 40 wt %, preferably about 35 wt %, abrasive particular material can have the same viscosity as conventionally formulated liquid abrasive household cleaners containing about 50 wt % particulate abrasive material. Use of the present thickening system in liquid abrasive cleaners can thus permit more flexibility in formulation. May abrasives can be used, but an abrasive which is particularly envisaged for use in household cleaning products is calcite. An abrasive should desirably have a particle size smaller than 150, better smaller than 100 micrometers.

Since calcite is able to react with acid, compositions containing it should be neutral or alkaline. A pH of 6.0 or greater is thus required with this abrasive; pH may well be 7.0, 8.0 or more.

Compositions according to this invention can also contain other ingredients such as builders including polymeric builders, sequestering agents, dyes, preservatives, perfumes, bleaches, bleach activators, solvents, enzymes, foam controlling agents and hydrotropes.

As well as household cleaning products, compositions within the scope of this invention include toothpastes.

In this respect, it has surprisingly been found that the inclusion of the synergistic mixture in toothpastes can provide toothpastes which have a higher gloss, a cleaner ribbon break and a smoother texture than toothpastes which have been thickened with the aid of current thickeners, e.g. sodium carboxymethyl cellulose. The present invention thus beneficially extends to a composition in the form of toothpaste containing 0.25 to 5 wt % of thickening mixture.

Preferred compositions according to this invention are formulated to have a viscosity at low shear (e.g. 10 sec $^{-1}$ shear rate) which is in a range from 100 mPa.s to 10 Pa.s.

The compositions of this invention can most readily be prepared by mixing together the constituent ingredients. The polymeric thickening agents can, but need not be, admixed together prior to addition to the liquid medium. In some instances, particularly those employing polymeric thickening agents all of which are derived from natural sources the mixture of thickening agents and liquid medium may require heating to yield a thickened liquid system. If heating is required the mixture is suitably held at between 85° and 95° C. for 1 to 15 minutes, or until no further thickening occurs.

The synergistic mixture can be added to the liquid media to be thickened in several ways, but care should be taken to avoid excessive aeration. We have found that a preferred way of incorporating the synergistic mixture into a liquid abrasive cleaning composition comprises the steps of adding the particular abrasive material to a dispersion of the thickening agents at alkaline pH, and thereafter adding the remaining ingredients of the composition.

The invention will further be illustrated by way of Example.

EXAMPLE 1

The viscosities at 10 sec$^{-1}$ of a linear gum-type polymer Maxaflo (ex International Bio-Synthetics) and of a branched starch-type polymer Amioca (ex National Starch and Chemicals Corporation) were each measured separately over a range of concentrations in respective aqueous solutions and as a mixture of the two polymers in aqueous solution over the same range of concentrations of one of the polymers whilst keeping the concentration of the other polymer constant.

Amioca is a starch derived from waxy maize and comprises 95% branched amylopectin glucose polymer molecules and 5% linear amylose molecules. Maxaflo is a very high molecular weight (>1,000,000) xanthan polysaccharide produced by a microorganism.

The results of measuring the viscosity of each polymer in separate aqueous solutions are given in Table I.

TABLE I

| Amioca (wt %) (pH 7) | Maxaflo (wt %) (pH 7) | Viscosity (mPa · s) ($10s^{-1}$) |
|---|---|---|
| 0.8 | — | 5.6 |
| 1.0 | — | 6.6 |
| 1.2 | — | 20 |
| 1.4 | — | 56 |
| 1.6 | — | 95 |
| 1.8 | — | 130 |
| 2.0 | — | 200 |
| — | 0.1 | 63 |
| — | 0.3 | 250 |
| — | 0.5 | 470 |

Figure 3:
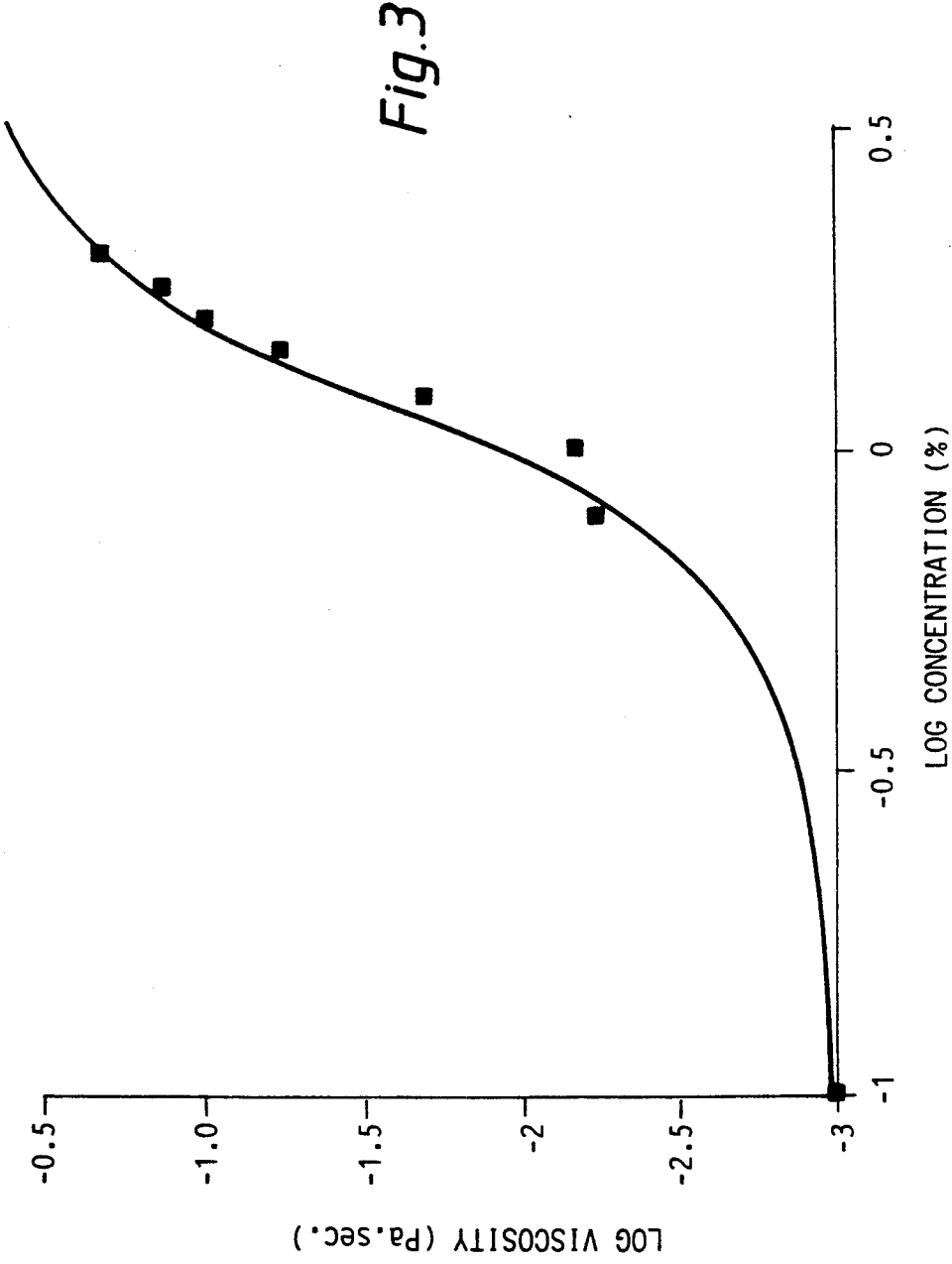

FIG. 3 is a plot of log viscosity v. log concentration for Amioca. The plot for Maxaflo is not shown but at 0.1 wt % the Maxaflo concentration lies in the required lower portion of the sigmoid curve.

In Table II below are the viscosity results at $10s^{-1}$ of a series of solutions containing a mixture of 0.1 wt % Maxaflo in combination with a range of concentrations of Amioca.

TABLE II

| Amioca (wt %) | Maxaflo (wt %) | Viscosity (mPa · s) | Synergy (%) |
|---|---|---|---|
| 0.8 | 0.1 | 130 | 88 |
| 1.0 | 0.1 | 145 | 108 |
| 1.2 | 0.1 | 165 | 99 |
| 1.4 | 0.1 | 190 | 60 |
| 1.6 | 0.1 | 240 | 52 |
| 1.8 | 0.1 | 240 | 24 |
| 2.0 | 0.1 | 280 | 6.5 |

Figure 4:
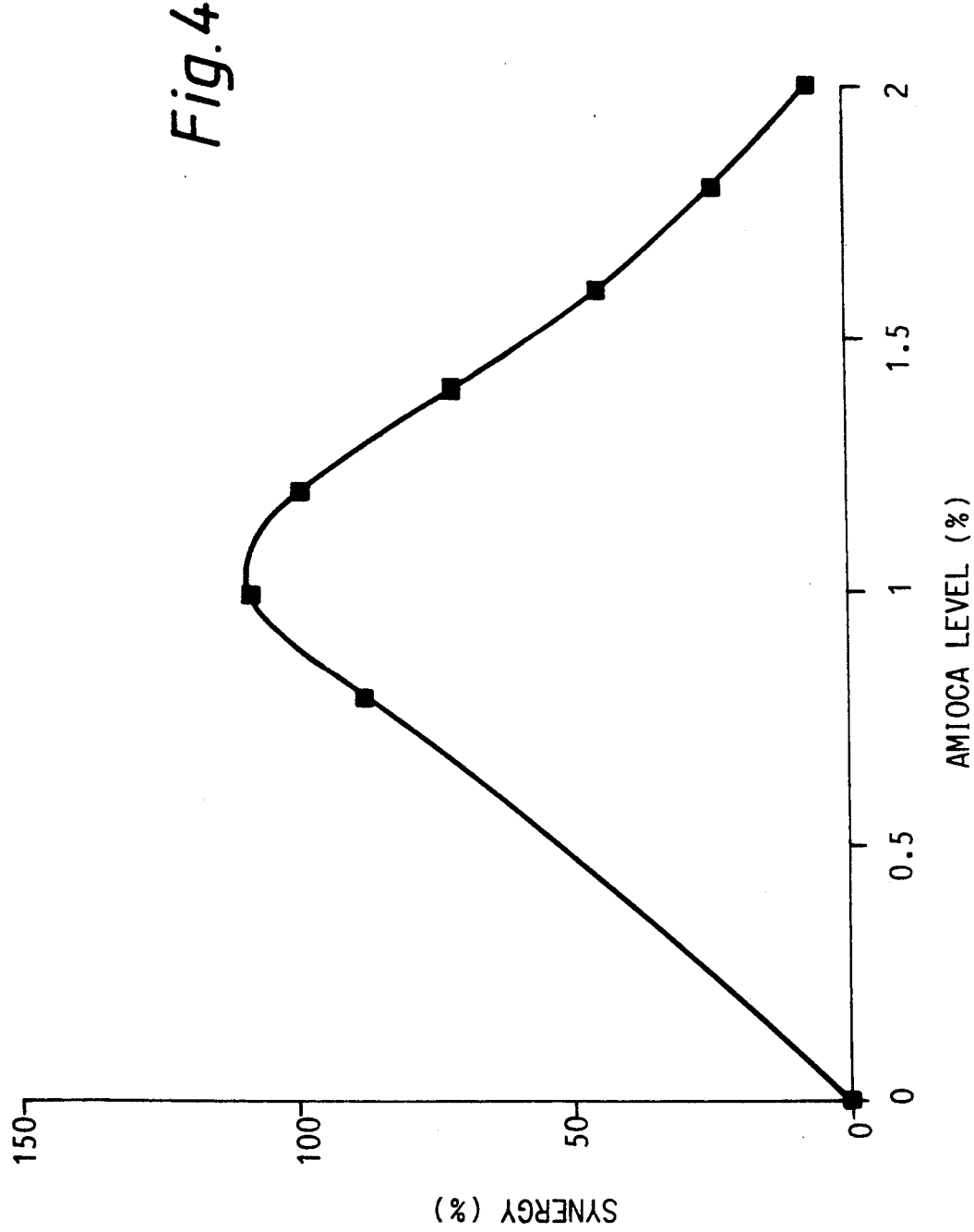

FIG. 4 illustrates in graphic form the synergy of the present thickening system and is a plot of synergy (S) as above defined against Amioca concentration.

EXAMPLE 2

Two formulations were prepared suitable for use as a liquid abrasive household cleaner employing as a thickening mixture a combination of Amioca and Maxaflo. The formulations are given in Table III below. Percentages are based on the whole composition.

TABLE III

| | A (wt %) | B (wt %) |
|---|---|---|
| Amioca | 3.2 | 2.8 |
| Maxaflo | 0.2 | 0.2 |
| Nonionic detergent (Dobanol 91-5T) | 1.5 | 0.0 |
| Potassium coconut soap | 0.0 | 2.0 |
| Abrasive (Calcite MM5F) | 35.0 | 35.0 |
| Perfume | 0.3 | 0.3 |
| Formalin | 0.1 | 0.1 |
| pH | 8.15 | 10.56 |

The viscosity stability of the two formulations was monitored over six months. The results are given in Table IV below.

TABLE IV

| | Viscosity (mPa-sec) ($21 sec^{-1}$) | |
|---|---|---|
| Months | A | B |
| 0 | 1800 | 1150 |
| 3 | 1735 | 1095 |
| 6 | 1690 | 1060 |

As can be seen, the stability was excellent.

Dobanol 91.5 T is $C_9$ to $C_{11}$ alcohol ethoxylated with average 5 ethylene oxide units and distilled to remove unreacted alcohol.

Particle size distribution of the calcite was

| 15% | <10 micrometers |
|---|---|
| 61% | 10 to 53 micrometers |
| 20% | 53 to 90 micrometers |
| 4% | >90 micrometers. |

EXAMPLE 3

Compositions were prepared containing various thickening materials in an aqueous liquid which also contained in every instance:

| Nonionic detergent ($C_{12}$ and $C_{13}$ alcohol ethoxylated with average 6.5 EO) | 1.5% |
|---|---|
| Perfume | 0.3% |
| Formalin | 0.1% |
| Calcite MM5F | 35% |

Again percentages were based on the whole composition.

The thickening polymers employed were Amioca starch, Maxaflo xanthan gum and Ultratex 4 starch (ex National Starch and Chemicals Corporation). This is a cold water swelling starch made from waxy maize starch in which about 95% is branched molecules (amylopectin).

The thickening materials and the viscosities at 10 $sec^{-1}$ shear rate were:

| Composition No. | Thickener | Viscosity (Pa · sec) at 10 $sec^{-1}$ | at 600 $sec^{-1}$ |
|---|---|---|---|
| 3A | {3% Amioca starch} {0.2% xanthan gum} | 2.9 | 0.320 |
| 3B | 4.5% Amioca starch | 3.9 | 0.52 |
| 3C | 3% Amioca starch | 1.6 | 0.24 |
| 3D | 0.5% Xanthan gum | 2.70 | 0.14 |
| 3E | 0.2% Xanthan gum | 0.80 | 0.059 |
| 3F | {2% Ultratex 4 starch} {0.2% Xanthan gum} | 3.5 | 0.22 |
| 3G | 3% Ultratex 4 starch | 4.5 | 0.440 |
| 3H | 2% Ultratex 4 starch | 0.75 | |

A disadvantage of composition 3D was that it had a stringy, unpleasant appearance when poured, making it unacceptable to consumers.

A comparative composition thickened with lamellar phase detergent was also prepared. This contained

| Alkyl benzene sulphate | 6% |
|---|---|
| Nonionic surfactant (as before) | 3% |
| Potassium coconut soap | 1% |
| Sodium carbonate | 4% |
| Calcite MM5F | 35% |

It had viscosities of 1.3 Pa-sec at 10 $sec^{-1}$ shear rate and 0.17 Pa-sec at 600 $sec^{-1}$ shear rate.

Some of the above compositions were tested for various properties, using the lamellar detergent composition as control.

Cleaning Test

A sheet of polymethylmethacrylate was soiled with a layer of microcrystalline wax. 1.5 ml of composition was applied to a damp sponge which was rubbed over the surface using an automatic machine, while a 300 gram weight pressed the sponge against the surface.

The number of rubs to remove the wax was recorded. The experiment was carried out twice. Results are quoted in Table V below.

Scratch Damage 1.5 ml of composition is applied to a damp sponge and rubbed over a sheet of clean, new polymethylmethacylate. The machine used for the cleaning test is used to carry out 50 rubs, with a 2 kg weight pushing the sponge onto the sheet. This was a pressure 120gm/cm$^2$.

The reflectance of the sheet is measured before the test and then after the test with a light path at 90° to the rubbing direction. The results are quoted in Table V below as reflectance after test divided by reflectance before test.

TABLE V

| Composition No. | Thickener | Cleaning Test Run 1 | Cleaning Test Run 2 | Scratch Test |
|---|---|---|---|---|
| Control | Lamellar phase | 52 | 52 | 0.84 |
| 3A | Amioca & xanthan | 29 | 26 | 0.87 |
| 3B | 4.5% Amioca | 40 | 39 | 0.89 |
| 3D | 0.5% xanthan | 24 | 30 | 0.87 |
| 3F | Ultratex & xanthan | 31 | 40 | 0.88 |
| 3G | 3% Ultratex | 40 | 47 | 0.90 |

As can be seen from Table V, the compositions 3A and 3F according to the invention performed better than most others in the cleaning test. In the scratch damage test they gave a better result than the control with lamellar phase detergent.

Only composition 3D did better in the cleaning test. The unacceptable appearance of this composition has already been mentioned.

We claim:

1. An aqueous liquid abrasive cleaning composition comprising an aqueous liquid medium containing detergent and a thickening mixture, with particulate abrasive suspended in the thickened liquid medium, the detergent being present in an amount of 0.02 to 20 wt. % based on the liquid medium, the particulate abrasive being present in an amount of 30 to 70 wt. % based on the liquid medium, and the thickening mixture being present in an amount of 0.01 to 10 wt. % based on the liquid medium and comprising a linear non-starch polymer and a branched starch polymer, wherein the two polymers are present in a weight ratio of linear non-starch polymer to branched starch polymer of between 20:1 and 1:25, and wherein each said polymer, when in said liquid medium in the absence of the other said polymer, has a relationship between concentration and viscosity, measured at a shear rate of 10 sec$^{-1}$ such that a graph of log (viscosity) against log (concentration) is a sigmoid curve with a lower position in which, over a range of concentrations, the gradient of the graph of log (viscosity) against log (concentration) is constant or increases with log (concentration), and wherein the amount of each of said polymers is such that the concentration thereof in the liquid medium lies within said range over which the gradient of that polymer's said curve of log (viscosity) against log (concentration) is constant or increasing, the thickened liquid system having a viscosity of at least 20 mPa-sec at a shear rate of 10 sec$^{-1}$ greater than that of the liquid medium in the absence of the said thickening mixture.

2. A composition according to claim 1 wherein the thickening mixture is present at a level between 0.25 and 5 wt % with respect to the liquid medium.

3. A composition according to claim 1 wherein the linear non-starch polymer is a synthetic polymer.

4. A composition according to claim 1 wherein the linear non-starch polymer is selected from the group consisting of xanthan gums, guar gums, succinoglucan gums, cellulose, and derivatives of any of these which include the polysaccharide polymer chain thereof.

5. A composition according to claim 1 wherein the liquid medium contains 0.1 to 10 wt % electrolyte.

6. A composition according to claim 1 wherein the thickening mixture imparts a synergistic increment S of at least 5% wherein S is defined as $$S = \left[ \frac{\eta(P_1 + P_2)}{\eta P_1 + \eta P_2} - 1 \right] \times 100$$

where $\eta(P_1+P_2)$=viscosity of a mixture of polymers $P_1$ and $P_2$ as measured for the said liquid medium $\eta P_1$=viscosity of polymer $P_1$ as measured for the said liquid medium $\eta P_2$=viscosity of polymer $P_2$ as measured for the said liquid medium.

7. A composition according to claim 6, wherein the two polymers are present in a weight ratio of linear non-starch polymer to branched starch polymer of between 20:1 and 1:25, wherein the thickening mixture is present at a level between 0.25 and 5 wt. % based on the liquid medium wherein the linear non-starch polymer is a synthetic polymer; and wherein the liquid medium includes 0.1 to 10% by weight electrolyte.

8. A composition according to claim 7, wherein the abrasive is calcite and the pH of the liquid medium is at least pH 7.0.

9. A composition according to claim 1 wherein the abrasive is calcite and the pH of the liquid medium is at least pH 7.0.

10. A composition according to claim 1, wherein the two polymers are present in a ratio of linear non-starch polymer to branched starch polymer of between 20:1 and 1:25, wherein the thickening mixture is present at a level between 0.25 and 5 wt. % based on the liquid medium wherein the linear non-starch polymer is a synthetic polymer; and wherein the liquid medium includes 0.1 to 10% by weight electrolyte.

11. A composition according to claim 1, wherein the amount of said detergent is 0.05 to 15 wt. % based on the liquid medium and the amount of thickening mixture is 0.5 to 1.5 wt. % based on the liquid medium.

12. A composition according to claim 1, wherein the branched starch polymer contains at least 70% of branched molecules.

* * * * *